(12) United States Patent
Green et al.

(10) Patent No.: US 10,000,779 B2
(45) Date of Patent: Jun. 19, 2018

(54) TWO-STAGE CONTINUOUS PROCESS FOR PRODUCING A SOLVENT

(71) Applicant: Green Biologics, Limited, Oxfordshire (GB)

(72) Inventors: Edward Green, Buckinghamshire (GB); Rosa Maria Dominguez-Espinosa, Berkshire (GB)

(73) Assignee: Green Biologics, Limited, Oxfordshire (GB)

( * ) Notice: Subject to any disclaimer, the term of this patent is extended or adjusted under 35 U.S.C. 154(b) by 429 days.

(21) Appl. No.: 14/416,259

(22) PCT Filed: Jul. 23, 2013

(86) PCT No.: PCT/GB2013/051955
§ 371 (c)(1),
(2) Date: Jan. 21, 2015

(87) PCT Pub. No.: WO2014/016576
PCT Pub. Date: Jan. 30, 2014

(65) Prior Publication Data
US 2015/0176035 A1 Jun. 25, 2015

(30) Foreign Application Priority Data
Jul. 23, 2012 (GB) .................................. 1213032.4

(51) Int. Cl.
*C12P 7/14* (2006.01)
*C12P 7/16* (2006.01)
*C12P 7/28* (2006.01)
*C12M 1/34* (2006.01)
*C12M 1/00* (2006.01)

(52) U.S. Cl.
CPC .............. *C12P 7/28* (2013.01); *C12M 21/12* (2013.01); *C12M 23/58* (2013.01); *C12M 41/26* (2013.01); *C12M 47/02* (2013.01); *C12M 47/10* (2013.01); *C12P 7/14* (2013.01); *C12P 7/16* (2013.01); *Y02E 50/10* (2013.01); *Y02E 50/17* (2013.01)

(58) Field of Classification Search
CPC ...... C12M 21/12; C12M 23/58; C12M 41/26; C12M 47/02; C12P 7/10; C12P 7/14; C12P 7/16; C12P 7/28; C12P 7/54; C12R 1/145
USPC ......... 435/150, 160, 161, 162, 252.7, 286.5, 435/842
See application file for complete search history.

(56) References Cited

U.S. PATENT DOCUMENTS 5,063,156 A 11/1991 Glassner et al.
5,753,474 A 5/1998 Ramey

FOREIGN PATENT DOCUMENTS

| DE | 3905624 | 9/1990 |
|---|---|---|
| EP | 1496108 | 1/2005 |
| GB | 2459756 A | 11/2009 |
| GB | 2457820 | 9/2010 |
| JP | 2008125456 | 6/2008 |

OTHER PUBLICATIONS

Ezeji et al. 2007. Bioproduction of butanol from biomass: from genes to Bioreactors. Current Opinion in Biotechnology, vol. 18, pp. 220-227.*
Godin et al. Two-stage continuous fermentation of clostridium acetobutylicum: effects of pH and dilution rate. Appl Microbiol Biotechnol (1990) 33: pp. 269-273.
Mutschlechner et al. Continuous two-stage ABE-fermentation using clostridium beijerinckii NRRL B592 operating with a growth rate in the first stage vessel close to its maximal value. J. Mol, Microbiol. Biotechnol. (2000) vol. 2, No. (1): pp. 101-105.
Richter et al. Prolonged conversion of n-Butyrate to n-Butanol with clostridium saccharoperbutylacetonicum in a two-stage continuous culture with in-situ product removal. Biotechnology and Bioengineering, vol. 109, No. 4, Apr. 2012, pp. 913-921.
Stephens et al. Studies on the stability of solvent production by clostridium acetobutylicum in continuous culture. Journal of Applied Bacteriology, vol. 58, No. 6 (1985) pp. 597-606.
International Search Report and Written Opinion for PCT/GB2013/051955 dated Oct. 15, 2013.
Fraleigh, Steven P., et al. Continuous culture, feedback control and auxostats. TIBTECH—Jun. 1989 vol. 7 pp. 159-164.
Green, E.M., et al. Biotransformations by *Clostridium beijerinckii* NCIMB 8052 in pH-auxostat culture. Appl Microbiol Biotechnol (1996) 44:553-556.
Lai, Mei-Chin, et al. A coupled two-stage continuous fermentation for solvent production by *Clostridium acetobutylicum*. Enzyme Microb. Technol., 1994 vol. 16 pp. 1021-1025.
Larsson, G., et al. The pH-auxostat as a tool for studying microbial dynamics in continuous fermentation. Biotechnology and Bioengineering, (1990) vol. 36, pp. 224-232.
Martin, Glenn A., et al. A Method for the regulation of microbial population density during continuous culture at high growth rates. Arch. Microbiol (1976), 107 pp. 41-47.
Masngut, Nasratun, et al. Performance of oscillatory flow reactor and stirred tank reactor in solvent fermentation from palm oil mill effluent. Jurnal Teknologi, 47 (F) Keluaran Khas. Dis. (2007) pp. 45-54. Universiti Teknologi Malaysia.

(Continued)

*Primary Examiner* — Louise W Humphrey
*Assistant Examiner* — Kailash C Srivastava
(74) *Attorney, Agent, or Firm* — Knobbe, Martens, Olson & Bear, LLP

(57) ABSTRACT

The present invention relates to a two stage continuous microbiological process for the production of solvents such as acetone, butanol and ethanol. The process involves the use of a solventogenic bacteria such as *clostridia*. In the first(acidogenic) stage, the culture vessel is fed with fresh growth media at dilution rates that support fast growth and acid production. The culture flows into the second (solventogenic) stage, which is a separate culture vessel or vessels, designed to provide the culture with sufficient residence time to convert acids into solvents. This vessel can be tubular or a series of linked batch vessels.

12 Claims, 10 Drawing Sheets

(56) References Cited

OTHER PUBLICATIONS

Minkevich, I.G., et al. Bisat—a novel method of continuous cultivation. Biotechnology and Bioengineering (1989), vol. 33, pp. 1157-1161.
Oltmann. Modification of the pH-auxostat culture method for the mass cultivation of bacteria. Biotechnology and Bioengineering (1978), vol. 20, pp. 921-925.
Rice, Craig W., et al. Nutrient-limited continuous culture in the phauxostat. Biotechnology and Bioengineering (1985), vol. 27, pp. 187-191.
Bahl, Hubert, Microbial production of butanol/acetone, Biotechnology. H.J. Rehm, VCH, Weinheim. p. 1-30 (1988).
Biebl, H., Comparative investigations of growth and solvent formation in 'Clostridium saccharoperbutylacetonicum' DSM 2152 and Clostridium acetobutylicum DSM 792, J. Industrial Microbiology and Biotechnology (1999) 22 p. 115-120.
Clarke, et al., Nature and significance of oscillatory behavior during solvent production by Clostridium acetobutylicum in continuous culture, Biotechnol. Bioeng. (1998) 32 p. 538-544.
Gapes et al., Long-term continuous cultivation of Clostridium beijerinckii in a two-stage chemostat with on-line solvent removal, Appl. Env. Microbial. (1996) 62: 3210-3219.
Godin, C. et al., Acid in the first stage is a determinant factor for the solvent production in the two-stage continuous fermentation of Clostridium acetobutylicum, Biotechol. Lett. 11: 903-906. 1989.
Jones, D. T. et al., Acetone-butanol fermentation revisited, Microbial. Rev. (1986) 50: 484-524.
Kashket, E.R. et al., Clostridial strain degeneration, FEMS Microbio. Rev. (1995) 17, 307-315.
Maddox, I., The acetone-butanol-ethanol fermentation: recent progress in technology, Biotechnol. Gen. Eng. Rev. (1989) 7, 189-220.
Maddox et al., Utilization of whey by clostridia and process technology, (1993) Woods, D.R. (ed), Butterworth-Heinemann, Boston. p. 343-369.
Ni, Y. et al., Recent progress on industrial fermentative production of acetone-butanol-ethanol by Clostridium acetobutylicum in China, Appl. Microbial. Biotechnol. (2009) 83, 415-423.
Qureshi, N. et al., Continuous solvent production from whey permeate using cells of Clstridium acetobutylicum immobilized by adsorption onto bonechar, Enz. Microb. Technol. (1987) 9 (11), 668-671.
Stephens, et al., Studies on the stability of solvent production by Clostridium acetobutylicum in continuous culture, J. Applied Bacteriology (1985) 59, 597-605.
Sun, Z.H., The design and technology of acetone-butanol continuous fermentation, Ind. Microbiol. 11, 31-37, 1981.
Woolley, R.C. et al., Stability of solvent production by Clostridium acetobutylicum in continuous culture: strain differences, J. Appl. Bateriol. (1990) 69: 718-728.

\* cited by examiner

TWO-STAGE CONTINUOUS PROCESS FOR PRODUCING A SOLVENT

Each of the applications listed in the accompanying Application Data Sheet is incorporated in its entirety by reference herein.

This application is the U.S. National Phase under 35 U.S.C. § 371 of International Application No. PCT/GB2013/051955, filed Jul. 23, 2013, designating the United States and published in English on Jan. 30, 2014, as WO 2014/016576, which claims priority under 35U.S.C. § 119 (a-d) to United Kingdom Application No. 1213032.4, filed Jul. 23, 2012.

The present invention relates to a two stage continuous microbiological process for the production of solvents such as acetone, butanol and ethanol. Preferably, the process involves the use of a solventogenic bacteria such as clostridia. In the first (acidogenic) stage, the culture vessel is fed with fresh growth media at dilution rates that support fast growth and acid production. The culture flows into the second (solventogenic) stage, which is a separate culture vessel or vessels, designed to provide the culture with sufficient residence time to convert acids into solvents. Preferably this vessel is tubular or a series of linked batch vessels.

A key feature of this invention relates to the method for controlling the flow of growth media into the first stage. Control is achieved by using a pH-Auxostat which not only maintains pH at a desired value but also provides an automatic or self-regulating mechanism to control the addition of fresh growth media (feedstock). This mechanism supports high dilution rates and fast growth rates of the microorganism in the first stage and high overall volumetric solvent productivities in the second stage.

The butanol fermentation process utilises renewable bio-based feedstocks and is often referred to as the acetone, butanol and ethanol (ABE) fermentation, after its major chemical products. The fermentation was first commercialised in the UK in 1916 and spread around the globe during the 1st and 2nd world wars, mainly to produce acetone for munitions and butanol for paint lacquers. The process fell out of favour in the US and EU in the 1950s when it struggled to compete with petro-derived equivalents on cost, but persisted in China, Russia and South Africa until the 1980s. Today, due to higher oil prices, concerns over the supply of oil and environmental concerns over greenhouse gas (GHG) emission, the ABE fermentation is poised for re-commercialisation. The fermentation route has the potential to replace petro-derived butanol, acetone and hydrogen with cheaper, more sustainable and environmentally-friendly chemicals. Indeed, global demand for bio-butanol has been stimulated by investment in new plant in China. Over $200 m has been invested to date, resulting in 0.3M t/yr of installed solvent capacity with plans to expand to 1 Mt/yr.

Traditional batch processes for the fermentation of molasses and/or starch to produce ABE have been practised for decades (Jones, D. T. and Woods, D. R. (1986) Microbiol. Rev. 50: 484-524). Typically, batch fermentation produces approximately 18 g/L solvent in 72 hours. The fermentation is relatively long because it occurs in two distinct stages: the first phase is a growth stage that results in acid production and a drop in pH; the second phase is a survival stage during which the acids are re-assimilated to solvents to neutralise the pH. The cells also prepare for sporulation. The switch in metabolism is triggered by the acid concentration in the fermentation broth and/or the drop in pH. In a typical fermentation, there is no control over the switch from acid to solvent production.

The solvent titres are relatively low in comparison with a yeast ethanol fermentation, and this results in low volumetric productivities (18/72 which equates to approximately 0.25 g solvent/L/hr). Low productivities are a major drawback with the traditional batch process and many attempts have been made to overcome this limitation. For example, variations on batch culture processes include fed-batch processes which attempt to either increase solvent titre or to reduce the fermentation time have been developed with little success.

Due to the low productivity obtained with batch fermentation processes, several single—stage continuous processes have been proposed (e.g. Jones and Woods (1986), supra) which aim to provide a continuous flow of feed media in order to achieve a growth rate close to the maximum growth rate for several weeks, thus offering improving solvent production rates and reduced downtime. However, in practice, this is difficult to achieve because solvent production is not directly linked to growth and cultures washout at relatively low dilution rates. Methods of retaining high cell concentrations in the reactor using cell-recycling and/or immobilisation have been demonstrated at lab-scales, but have been difficult to implement on commercial scales (e.g. Qureshi & Maddox (1987), Enz. Microb. Technol. 9(11), 668-67; Maddox (1989) Gen. Eng. Rev., 7, 189-220; Maddox et al. (1993) In: The clostridia and biotechnology, (eds) D. R. Woods, Butterworth-Heinemann, Boston. 343-369; Gapes et al. (1996) Appl. Env. Microbiol. 62: 3210-3219). Other continuous configurations based on two- or multi-stage vessels have been proposed in an attempt to separate and control the biphasic fermentation but none have proved successful due to difficulties in controlling the flow rates and corresponding dilution rates to maximise solvent productivity (see below).

A two-stage sequential fermentation processes for first butyric acid fermentation and butanol fermentation using two different microbes has been described by Ramey (U.S. Pat. No. 5,753,474). The first step involves the continuous fermentation of carbohydrates into butyric acid using C. tyrobutyricum. The second step is the conversion of butyrate (with a small amount of sugar) to solvents (acetone, ethanol and butanol) using a second (different) solventogenic Clostridia strain. This is a complicated system involving two different microbes that are immobilised to prevent culture washout. In practice, this fermentation is difficult to control and scale-up to commercial volumes.

Most of the developments for two-stage Clostridia continuous cultures with one microbe focus on acid production during the first process stage and solvent production in the second stage but this strategy generally fails because mixed cell populations of acidogenic and solventogenic cells quickly build up in both the first and second stage providing oscillations in growth and solvent formation. For free cell suspensions if flow rates are not controlled, this typically results in cultures that washout if growth slows or sub-optimal growth if flow rates are kept low. In addition, cultures tend to degenerate quickly losing the ability to produce solvents (Woolley and Norris (1990) J. Appl. Bacteriol. 69: 718-728; Jones and Woods, (1986) supra; Kashket and Cao (1995), FEMS Microbiol. Rev., 17, 307-315; Afschar (1990) DE 3905624 A1). For example, Afschar (1990) proposed a two stage molasses fermentation process for the production of butanol and acetone, which is characterized by a chemostat with substrate limitation at the first stage to produce cells. A two-stage continuous cultivation for clostridia was also proposed by Mutschlechner et al. (J. Mol. Microbiol. Biotechnol. (2000) 2(1):101-105). In this process, the system was designed to mimic the two phases of batch culture growth by using a first stage to grow the cells acidogenically as fast as possible and then transferring cells to the second stage at the 'acid break point'. The second vessel is larger to provide sufficient residence time to complete solvent production. In both these examples, the flow rates into the first and second stage were kept constant and not regulated in response to any growth related signals such as changes in pH or cell density.

Two-stage continuous cultures have also been described with immobilized biomass or cell-retention (e.g. Maddox et al. (1993), supra; Gapes et al. (1996), supra). These authors have used a fixed dilution rate and describe immobilisation methods to retain the microbes in the reactor and to prevent them from washing out. These cultures can be run at high dilution rates and productivities but the final solvent concentrations tend to be too low for cost-effective recovery. Also, in both examples, solvent titres and productivity oscillated widely. The main drawback with immobilisation is the expense and difficulty to scale. Operation over prolonged periods and/or use of feedstocks with particulates is problematical due to blockages and fouling of the support matrices. In addition, these systems are prone to contamination and difficult to keep sterile.

A sequential fermentation process has been commercialised in China wherein a continual or sequential batch process is used with eight fermentors linked together. The first two vessels (vessels 1 and 2) are biomass generators and are continuously re-seeded with fresh culture every 24 hours (via a conventional seed train). The biomass generators, once seeded, are fed continuously with substrate (feedstock) and, when full, the liquid flow goes forward to vessels 3 and 4 (which work in parallel). These two vessels then feed the rest of the fermentation train, which consists of a sequential series of connected vessels (usually four) giving a total process residence time of 72 h in the eight fermentation vessels. This complicated process has been designed around the limitations of *C. acetobutylicum* which generally requires continual re-seeding to avoid microbe degeneration (due to loss of solvent plasmid). This process is controlled manually, with very little scope to respond quickly to process fluctuations. The continual Chinese process is described in Ni & Sun (2009), Appl. Microbiol. Biotechnol., 83, 415-423.

A single stage continuous culture method based on a pH-Auxostat has been described in the literature. Martin and Hempfling (Arch. Microbiol. (1976) 107(1), 41-47) and Oltmann et al. (Biotechnol. Bioeng. (1978) 20(6), 921-925) proposed methods for the continuous culture of microorganisms which employs growth-dependent pH changes to control the rate of addition of fresh medium to a culture vessel. Their "pH auxostat" has the potential to sustain continuous cultures at growth rates very close to the maximum growth rate for the strain at the given conditions. The buffering capacity of the feed medium determines the steady-state population density of the culture. This is a fundamental difference from the traditional chemostat or turbidostat cultures, where the growth rate is determined by the rate of addition of culture medium containing a limiting amount of a substance required for growth. However, the application of the pH-auxostat for two-stage butanol fermentation has not previously been proposed due to the biphasic nature of Clostrida growth and solvent production. Indeed, in batch culture solvent production and most solvent production occurs when growth slows or even stops. Biebl ((1999) J. Industrial Microbiology and Biotechnology, 22(2), 115-120) describes a single stage pH-auxostat method for the solvent production by Clostridia (using a method described by Oltman, 1978). The author found that solvent production decreased rapidly when dilution rates increased above $0.1\ h^{-1}$.

Stephens et al. (J. Appl. Bact (1985) 59,597-605) also describe a single stage pH-auxostat method for the solvent production by Clostridia based on the method of Oltman, 1978 (supra). Solvent concentrations fluctuated and were relatively low. True steady state conditions were not achieved during the fermentation. Later, Green and Stephens (Appl. Microbiol. Biotechnol. (1996) 44: 53-556) describe a variation of the single stage pH-Auxostat method to maintain Clostridia in either an acidogenic or solventogenic growth mode by manipulating the sugar concentration. At low sugars (10 g/L), the cells produced predominantly acids whereas at higher sugar concentrations (30 g/L) the cells produced solvents albeit at low yield and titre. In this study, the pH-auxostat was used as a research tool to investigate the potential of Clostridia to mediate reductive biotransformations. The authors made no attempt to optimise growth or solvent production in this culture system.

None of the work prior done with Clostridia describes how the pH-auxostat might be used to increase solvent productivity. In fact, the results generated teach away from using this technique in a single stage process for producing solvents at high dilution rates. In addition, steady state conditions were not demonstrated.

Variations on the pH-auxostat have been described by Richter et al. (Biotechnol. Bioeng. (2012) April; 109 (4): 913-21) who deployed a two stage continuous culture. Both stages were fed at fixed dilution rates and the pH-auxostat was only used to control the addition of butyric acid to stage 2 in an attempt to improve butanol yield.

A single stage turbidostat culture has also been described by Stephens et al. (1985, supra). Solvent concentrations fluctuated and were relatively low. Turbidostats permit continuous cultivation at a selected biomass which is monitored by instrumentation linked to the feed pump. When the cell density falls before the set level the feed pump is triggered to produce more nutrients to support cell growth. Since turbidostat cultures rely on accurate measurements of cell density, this means, in practice, that they are extremely difficult to measure in situ over a prolonged period of time, especially if there are any particulates in the growth media. Also, in principle, turbidostat control is similar to the pH auxostat control. It is difficult to use either method to produce solvents in a single stage process since solvent production in clostrida is not linked to growth.

In contrast, the process of the current invention employs the pH-auxostat in stage one of a two-stage process. The pH-auxostat is used to automate control of the dilution rate in response to fluctuations in growth (not fixed) and is configured to produce a supply of fast growing and metabolically-active cells that feed a second stage optimised for solvent production. The primary objectives of this process are to improve dilution rate and maintain high solvent productivity over a prolonged period of time. The process is simple, scalable, easy to operate and automatic with self-regulating control of dilution rate. In this process, the two metabolic phases are separated and the switch from acid to solvent production is controlled. Decoupling acid and solvent production in this way means that the two parts of the fermentation process can be optimised and controlled separately, i.e. at different pH or temperature values. An additional advantage is that changes can be made to stage 2 without affecting the growth and supply of viable cells (from stage 1). For example, 1) cells may be recycled back into the vessel from the solvent recovery process to increase cell density and solvent titres; 2) additional sugars and nutrients may be fed into the vessel to improve solvent titre (this may be controlled using a second pH-auxostat); and 3) the solvents could be stripped directly from the vessel and concentrated to assist with the recovery process. Furthermore, since the system is self-regulating, the culture should not wash out if growth is inhibited due to fluctuations in feedstock composition. In practice, this means that solvent producing cultures can be maintained for long time periods.

The invention therefore provides a two-stage process for the production of a solvent using an acid- and solvent-producing micro-organism, comprising the steps:

(i) culturing the micro-organism under acidogenic conditions in a liquid medium in a first culture vessel, wherein the pH of the liquid medium in the first culture vessel is controlled by a pH auxostat, and wherein the flow rate of fresh media which is introduced into the first culture vessel is also controlled by a pH auxostat;

(ii) transferring a portion of the liquid medium from the first culture vessel to a second culture vessel or series of linked culture vessels; and (iii) culturing the same micro-organism under solventogenic conditions in the second culture vessel(s) for a time which is sufficient for solvent to be produced, and optionally isolating one or more solvents which are produced in the second culture vessel(s). Preferably, the process is a continuous or semi-continuous process.

In Step (i) of the process, the micro-organism is cultured under acidogenic conditions in a liquid medium in a first culture vessel, wherein the pH of the liquid medium and the control of fresh media into the first culture vessel is controlled by a pH auxostat.

The aim of the first stage is to supply exponentially growing cells at high feed rates and at the same time avoid any strain degeneration or instability. In the first culture vessel, the micro-organism is cultured under acidogenic conditions, hence no or essentially no solvent is produced in first stage. The acidogenic conditions are maintained at relatively high pH values and high dilution rates using a pH auxostat, whereby growth-dependent pH changes in the culture are controlled by the addition of fresh medium and alkali to the culture vessel.

In the first stage, the feed rate (or dilution rate) is automatically controlled by the pH auxostat in response to the rate of cell growth and acid production. In practice, faster growing cells produce more acid which in turn results in faster feed rates. The feed may therefore be continuous, semi-continuous or intermittent.

The micro-organism to be used in the process is one which is capable of producing acids and converting them into solvents. The micro-organism may be a biphasic micro-organism. As used herein, the term "biphasic" refers to a micro-organism which has an acidogenic growth phase and a solventogenic growth phase.

The term "acidogenic growth phase" refers to the ability of the micro-organism to convert a substrates based on sugars and starches into RCOOH (wherein R is as defined below), for example, into acetate and/or butyrate.

The term "solventogenic growth phase" refers to the ability of the micro-organism to convert the RCOOH into a solvent, preferably into one or more of acetone, ethanol and/or butanol.

In some embodiments, the micro-organism is preferably a bacterium, for example a gram-positive or gram-negative bacterium. In some embodiments, the micro-organism is a spore-forming bacterium. The micro-organism may be an aerobic or an anaerobic micro-organism. Preferably it is an anaerobic or aero-tolerant micro-organism. Most preferably, it is an aero-tolerant bacterium.

The acid- and solvent-producing micro-organisms which are used in the first culture vessel may be from a single strain or from a co-culture, preferably a single strain. The micro-organisms which are used in the first culture vessel are the same micro-organisms which are used in the second culture vessel.

In some embodiments, the micro-organisms are acid-tolerant. The micro-organisms can preferably tolerate high concentrations of COOH. In this context, high concentrations of COOH may mean up to 15 g/L acetic acid, and/or up to 10 g/L lactic acid and/or up to 6 g/L formic acid.

Preferred solventogenic micro-organisms include solventogenic *Clostridium*. Preferred acetone/butanol-producing species are *C. acetobutylicum, C. beijerinckii, C. saccharobutylicum* and *C. saccharoperbutylacetonicum*. Preferred isopropanol/butanol producing strains are *C. pasteurianum*.

Preferably, the micro-organism is *Clostridium acetobutylicum* or *Clostridium beijerinckii, C. saccharobutylicum* and *C. saccharoperbutylacetonicum*. Within each species group are preferred strains. Preferably, the micro-organism is an acid-tolerant *Clostridium*. In a particularly preferred embodiment, the micro-organism is *C. saccharoperbutylacetonicum* or *Clostridium beijerinckii*.

In some embodiments, the micro-organisms may be immobilised. In other embodiments, the micro-organisms are non-immobilised or are in free suspension. This applies independently to both the first and second culture vessels.

The micro-organisms in the first culture vessel are maintained under conditions which are suitable for them to produce acids. Such conditions are well known in the art. The conditions will include the provision of nutrient media comprising appropriate carbon sources, for example assimilable carbohydrates.

Examples of assimilable carbohydrates are sugars such as C5 and C6 monomers, C5 and C6 sugar dimers, and sugar polymers. Preferred sugars are arabinose, xylose, mannose, fructose, glucose, galactose, sucrose, lactose, maltose, cellobiose. Preferred polymers are starch, xylan, pectin, fructan, cellulose and mannitol. Another suitable carbon source is glycerine.

Preferably, sugars are hydrolysates derived from lignocellulosic feedstocks such as corn residues, sugar residues, woody residues or municipal waste. Other suitable feedstocks include agriculture by-products and process wastes.

The feedstock may comprise multiple or blended feedstocks. In its simplest form, the nutrient media may contain sufficient sugar and nutrients so that a surplus would transfer to the second culture vessel. In practice, this means feeding sugar concentrations between 1 and 10% w/v to the first culture vessel. Additional sugar may be fed into the second vessel at the same concentration (e.g. 1-10%) or higher (e.g. 10-50%).

The pH of the culture vessel(s) may be controlled through the addition of alkali from a separate alkali feed or from the addition of feed media that has a pH lower than the culture vessel(s) (typically 1-2 pH units). Preferably, the pH-auxostat has a separate alkali feed and the pump is linked to the pump controlling the media feed.

The pH of the culture, the buffering capacity of the fresh media, the type and concentration of alkali added to the first culture vessel are selected so as to maximise the growth rate and population density of the cultured organism using a pH auxostat. The cell density in the culture vessel(s) may be controlled by altering the ratio or relative speed of the alkali-feed and media-feed pumps.

pH auxostats are known in the art (e.g. Martin & Hempfling (1976), Arch. Microbiol. 107, 41-47). In such pH auxostats, the buffering capacity of the inflowing medium determines the steady-state population density of the culture, but the rate of growth is independent of the buffering capacity; and the specific growth rate of the micro-organisms is very close to $\mu_{max}$.

The pH auxostat maintains the pH of the medium in the first culture vessel at a predetermined level by controlling/regulating the addition of fresh media and alkali to the culture vessel. Hence the pH auxostat maintains the micro-organism in its acidogenic phase in the first culture vessel. In this process, the ratio between the flow rates of the fresh medium and that of alkali determines the steady-state population density of the micro-organisms in the first culture vessel, thus allowing the micro-organisms to grow at the maximum specific growth rate that is possible in that medium.

In general, this means controlling the pH at a set value and linking the pumps for alkali and media together so that they respond simultaneously, so that alkali and fresh media are added simultaneously to the first culture vessel. The media and alkali pumps are both triggered simultaneously once the pH drops below the set value and will continue until the pH is restored. In practice, this means they are triggered intermittently but additions will become regular (i.e. semi-continuous) once the culture stabilises. The alkali and fresh media may be added into the first culture vessel in the same stream or independent streams, preferably in separate streams.

Over time, the culture should regulate fresh media additions in response to any changes in media composition. For example, if growth slows, the pH will fall slower and the rate of addition of fresh media will drop. Conversely, if growth is fast, the pH will drop quicker and the fresh media addition rate will increase. An advantage of this is that, if a feedstock inhibitor is present, the culture will not wash out and over time.

Further control can be achieved by varying the rate of addition (pump speed) and/or varying the concentration of alkali, as is known in the art.

In its simplest form, the pH auxostat comprises a pH sensor, a pump or pumps and electronic means (e.g. a computer) to operate the pump(s) when the pH falls below a predetermined level.

Over time, if growth conditions are favourable, the culture in the first culture vessel will grow close to its maximum growth rate ($\mu_{max}$). Unlike a conventional chemostat culture with a fixed dilution rate, the culture in a pH auxostat should not wash out if growth slows (possibly due to growth inhibitors in the feed, for example) and will generally adapt and recover making it a good system for fermenting feedstocks that may contain inhibitory components, e.g. cellulosic feedstocks.

The pH of the first culture vessel is preferably pH 5.5-7.0, more preferably pH 5.5-6.5.

The temperature will be selected as being one at which the micro-organism grows best. For example, for mesopholic Clostridria, the temperature is preferably 30-37° C.

The process of the invention is preferably operated under continuous culture conditions. As used herein, the term "continuous culture conditions" refers to a process wherein the culture of micro-organisms in the first culture vessel is capable of being maintained with a continuous or substantially continuous flow of feed in steady state conditions and at high growth rates (greater than 50% $\mu_{max}$) for prolonged periods of time. Preferably for at least 7 days or longer.

The first culture vessel may be any form of culture vessel which is suitable for culturing the micro-organisms of the process of the invention. Preferred types of culture vessel include conventional stirred bioreactors.

In some embodiments of the invention, a continuous seed generation system is used, feeding the first culture vessel or vessels. Preferably, the first culture vessel is not reseeded (after the initial culture seeding).

In Step (ii) of the process, a portion of the liquid medium from the first culture vessel is transferred to a second culture vessel. The liquid medium will also in general contain viable micro-organisms and optionally surplus sugar and/or nutrients from the first culture.

The first culture vessel is connected directly or indirectly to the second culture vessel(s), thus allowing passage of liquid media from the first to the second culture vessel(s). This liquid media will be enriched in the acids which are produced in the first culture vessel by the micro-organisms.

Preferably, the first culture vessel is connected directly to the second culture vessel(s), wherein liquid media is transferred continuously from the first to the second culture vessel(s).

In some embodiments, the first culture vessel is connected indirectly to the second culture vessel(s), thus allowing less than the maximum flow rate of liquid medium to be transferred to the second culture vessel(s).

Preferably, the feeding rate for the first culture vessel (as controlled by the pH auxostat) and the flow rate from the first to the second culture vessels are the same. This rate is preferably self-controlled by the growth rate of the culture in the first culture vessel (which may, for example, correspond to dilutions rates for the first vessel of 0.10-0.5 h$^{-1}$). This equates to residence times of between 2 and 10 hours.

In Step (iii), the micro-organism is cultured under solventogenic conditions in a second culture vessel. This second culture vessel(s) are independent from the first, i.e. they are separate vessels to the first vessel. In this stage of the process, the acids which were produced in the first culture vessel are converted to solvents in the second culture vessel(s).

The micro-organisms in the second culture vessel are maintained under conditions and for a time which is suitable for them to produce solvents. Such conditions are well known in the art.

The total volume of the second culture vessel(s) should be sufficiently large enough to provide enough residence time for the micro-organisms to convert all or substantially all of the acids to solvents based on the flow rate of fermentation broth exiting the first culture system. Preferably, the residence time in the second culture vessel should be between 2 and 24 hours, most preferably about 10 hours.

The pH of the second culture vessel(s) is preferably pH 4.5-6, more preferably about pH 5. The pH many not be regulated. In some embodiments, the pH may be controlled at a set value using a pH-auxostat. Under this scenario, the pH would be kept below a set value with acid additions.

The temperature will be selected as being one at which the micro-organism produces most solvent. For example, for mesopholic Clostridria, the temperature is preferably 30-37° C.

In general, the second culture vessel(s) are not fed with additional media; enough sugar and nutrients for the microorganisms to grow and produce solvents is passed from the first culture vessel. However, in some embodiments, the second culture vessel(s) are also fed with an independent nutrient feed containing sugar and/or nutrients. This could be fed at a constant flow rate or controlled by a pH auxostat.

In some embodiments, it may also be desirable to concentrate the cells in the second culture vessel(s) using cell recycling with membranes and/or centrifugation. In this process configuration, cells are separated from a portion of the liquid medium which has been removed from one or more of the second culture vessels, and the cells returned to one or more of the second culture vessels. The remaining liquid may then be passed to a solvent recovery system.

In some embodiments, it may also be desirable to seed the second culture vessel(s) with the micro-organism in order to maintain some growth in the second vessel(s).

The micro-organism which is used in the second culture vessel(s) is the same as that which is used in the first culture vessel.

As used herein, the term "solvent" or "solvents" refers to low boiling point organic solvents or their azeotropes which are capable of being produced by solventogenic micro-organisms in a liquid fermentation medium. Examples of such solvents include alcohols of formula R—OH, wherein R is an aliphatic C1-C8 alkyl group or an aliphatic C2-C8 alkenyl group. The R group may be branched or linear. Preferably, it is linear. The R group may be saturated or unsaturated. Preferably it is saturated.

Preferred examples of alcohols of formula R—OH include methanol, ethanol, 2 methyl-propan-1-ol, 1,3-propanediol, 1-butanol, 2-butanol, 2-methyl propan-2-ol, pentanol, hexanol, heptanol and octanol. A further example of a solvent has a formula R—CO including acetone (($CH_3$)$_2$ CO). Preferably, the solvents comprise ABE solvents, i.e. acetone, 1-butanol and ethanol. Most preferably, the solvents comprise 1-butanol or substantially 1-butanol.

The temperature in the second culture vessel(s) is preferably between 30-37° C.

In some embodiments of the invention, the cell density of the micro-organism in the second culture vessel(s) is controlled by a turbidostat.

The design of the second culture vessel(s) can be any form which provides sufficient residence time for the cells to re-assimilate all or essentially all of the acids in the liquid medium and to convert them into solvents. Examples include a long tubular vessel (with or without baffles), a series of linked batch vessels or a single batch vessel (preferably of greater volume than the first culture vessel).

In one preferred embodiment, the second culture vessel is a long tube or a series of tubes. The tubes may, for example be made of glass or metal. Preferably, in the tube format, the culture flows in plugs with each plug having a uniform composition ("plug flow"). The key assumption is that as each "plug" of culture flows through the reactor, the fluid is mixed in the radial direction but not in the axial direction (forwards or backwards). Plug flow reactors may be simple tubes or have baffles to aid mixing. Such reactors are well known in the art for chemical synthesis but not for microbial fermentation. They can also comprise a series of linked batch vessels.

The second culture vessel may alternatively be a series of linked or sequential batch fermentors (e.g. Chinese continual process). For example, the second culture vessel may comprise 1-8, preferably 4 batch reactors, which may be used in sequence. In this example, one of the four batch production vessels (typically 300-400 m$^3$) could be reconfigured to run as a pH-auxostat and used to seed the other three vessels arranged in series or cascade.

In its simplest form, the second culture vessel may be a single batch vessel with a sufficiently large volume differential to provide sufficient residence time. For example, on a Chinese butanol plant, the 30-60 m$^3$ seed vessel could be reconfigured to run as an auxostat and then used to seed one of the larger production vessels or fermenters (which may accommodate up to 400 m$^3$).

After passage through the second culture vessel(s), the solvents produced therein may be recovered from the solvent-containing liquid medium by any suitable process. Generally, the solvents will be recovered from the fermentation broth by one or more of liquid-liquid extraction, gas stripping, vacuum evaporation, vacuum distillation, pervaporation, ion-exchange adsorption, counter-current solvent extraction and/or distillation. Alternatively, hydrophobic membranes may be used, e.g. with air flux or inert gas carrier or vacuum (pervaporation) to aid the separation (preferably in a continuous process). Preferably, primary extraction will be performed by a method that can be used to remove solvents in situ during the second stage. In other preferred embodiments, the solvent extraction may be a continuous solvent extraction process.

The invention also relates to a solvent which is obtained by a process of the invention.

The invention also provides a system for the production of a solvent, the system comprising:
(i) a first culture vessel which contains or is adapted to contain a liquid medium suitable for acidogenic growth of an acid- and solvent-producing micro-organism,
(ii) one or more second culture vessels which contain or are adapted to contain a liquid medium suitable for solventogenic growth of the acid- and solvent-producing micro-organism, and
(iii) a pH auxostat, wherein the pH auxostat is arranged to control the pH of the liquid medium in the first culture vessel, and wherein the first and second culture vessels are in liquid communication.

The micro-organism is preferably one as defined herein. The liquid medium of the first and/or second culture vessels may additionally comprise the micro-organism, preferably growing in acid- or solvent-producing growth mode, respectively.

Preferably, the pH auxostat comprises a pH sensor, a pump or pumps, and electronic means (e.g. a computer) to operate the pump(s) when the pH in the first culture vessel falls below a predetermined level.

The system may additionally comprise a vessel which contains or is adapted to contain an alkali; and a vessel which contains or is adapted to contain fresh culture media. These latter vessels may be in liquid communication with the first culture vessel.

The means for liquid communication preferably comprises a pipe.

The second culture vessel(s) are preferably in the form of a long tubular vessel (with or without baffles), a series of linked batch vessels or a single batch vessel (preferably of greater volume than the first culture vessel). The vessels may be linked in series or in parallel.

The system may additionally comprise a cell separator which is arranged to act on a portion of the liquid media which been removed from the second culture vessel(s); to separate cells from the liquid media in that portion; and optionally to return the cells to the second culture vessel(s). The cell separator may be in liquid communication with the second culture vessel(s).

The system may additionally comprise means for separating one or more solvents from liquid medium. Preferably, the solvent(s) will be recovered from the liquid medium by liquid extraction means, gas stripping means and/or distillation means.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. The disclosure of each reference set forth herein is incorporated herein by reference in its entirety.

Example 1

Single Stage pH-Auxostat

Objective:
To demonstrate a method to continuously cultivate Clostridia at high dilution rates. The method was based on a pH-Auxostat (FIG. 1) and was focused on the production of an actively growing cell population at or close to its maximum growth rate.

Materials and Methods

Bacterial Strain

A solventogenic Clostridium beijerinckii strain was cultured on a standard anaerobic culture medium such as reinforced clostridial medium (RCM) in 100 mL serum bottles under anaerobic conditions at 32° C.±1° C.

| RCM semi-solid medium composition in g $L^{-1}$ | |
|---|---|
| Yeast extract | 3.0 |
| Lab-Lemco powder | 10.0 |
| Peptone | 10.0 |
| Glucose | 5.0 |
| Soluble starch | 1.0 |
| Sodium chloride | 5.0 |
| Sodium acetate | 3.0 |
| Cysteine hydrochloride | 0.5 |
| Agar | 0.5 |
| *pH | 6.8 ± 0.2 |

*Adjusted as required to meet performance standards, sterilised by autoclaving at 121° C.

Culture Medium

Thick juice from beet sugar (obtained from a sugar mill) was the main carbon source for the fermentation media. Experiments were carried at two sugar concentrations 25 g $L^{-1}$ or 45 g $L^{-1}$ supplemented corn steep liquor 5 g $L^{-1}$, 4 g $L^{-1}$ Tryptone, 2 g $L^{-1}$ yeast extract and 0.05 g $L^{-1}$ $FeSO_4$. When needed, pH was adjusted with 20% w/v of NaOH to a pH of 7.0. All mineral salts were laboratory grade (Fisher Scientific).

Figure 1:
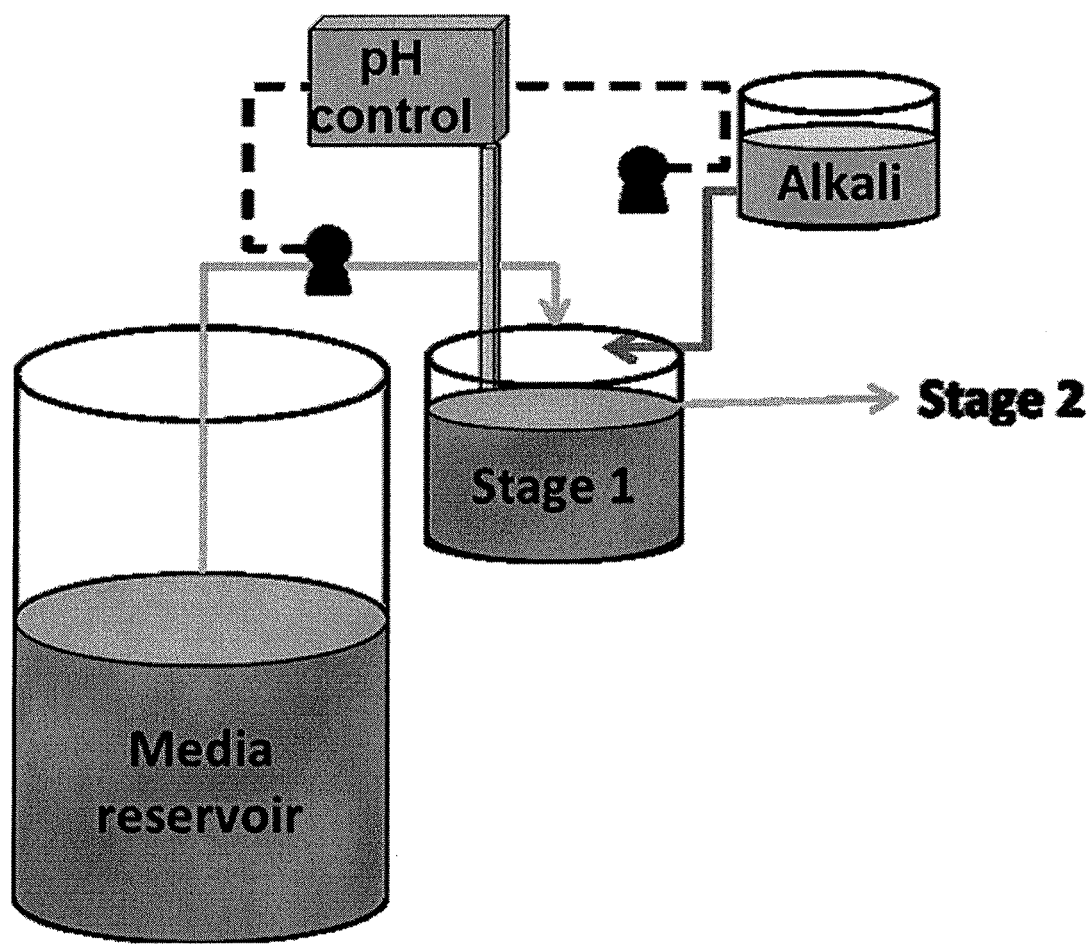
FIG. 1. Single stage pH-Auxostat system for continuous cultivation of Clostridia at high dilution rates.

Culture Conditions pH-Auxostat fermentations were carried out in 1 L fermenters with working volumes of 0.7 L. The fermenters were equipped with gas exhaust, stirrers, sampling ports, pH and temperature sensors. They were initiated as batch cultures with the inoculation of 5% v/v seed culture. The feeding vessel (20 L) was connected to the fermenter immediately after inoculation (FIG. 1). Auxostat-mode operation was started approximately 10-14 h after inoculation. The alkali feed pump and media reservoir pump were linked and activated simultaneously once the pH in the vessel falls below the set value. The medium reservoir supplied fresh sugar and nutrients. The alkali pump and feed pumps ran automatically and intermittently depending on growth rate and culture pH. A control system was fitted to maintain temperature at 30° C. and minimum agitation (50-70 rpm). The alkali agent used was NaOH (range 2-10%). Alkali additions neutralized the culture pH to the set pH value of 6 (pH range 5.5-6.5).

The culture could be sparged with $N_2$ or $CO_2$ to maintain anaerobic conditions. However no special precautions were taken to exclude/remove oxygen.

Analysis of Products and Substrates

Growth was monitored at 600 nm by a Jenway 6300 spectrophotometer with cuvettes of 1 cm light path. Cultures were diluted if necessary so that the absorbance did not exceed 0.6 units.

Concentrations of acetate, butyrate, ethanol, acetone, and n-butanol were measured by applying the supernatant from centrifuged fermentation samples to gas chromatography on an Agilent Gas Chromatography system with a network headspace sampler. The equipment was fitted with a capillary column (Agilent 19091F-115E HP-FFAP) with a column temperature ramp from 80° C. up to 200° C. The carrier gas was $N_2$ with a flow rate between 0.8 mL/min and 1.3 mL/min. The FID detector temperature (300° C.) operated with a hydrogen flow at 50 mL/min and air flow at 400 mL/min and make up flow ($N_2$) at 30 mL/min. Iso-butanol (99.5%) and iso-butyric acid (99.5%) at concentrations of 1 g/100 mL each of HPLC grade water were used as internal standards.

The sugar content of the fermentation samples was determined by high pressure liquid chromatography using a Dionex HPLC fitted with auto sampler (ASI00) and a Shodex RI-101 refractive index and UV detector. The separation column was COREGEL-87C and operated at 85° C. HPLC grade water was used as mobile phase at a flow-rate of 0.6 mL/min. The sample injection volumes were 10 μl. The calibration curve was created by integrating the peak areas from chromatograms generated from solutions of sucrose, D-glucose, and D-fructose mixtures at concentrations of 0.5, 1, 10, 15, 20 and 25 g $L^{-1}$ of each sugar.

Results

Figure 2:
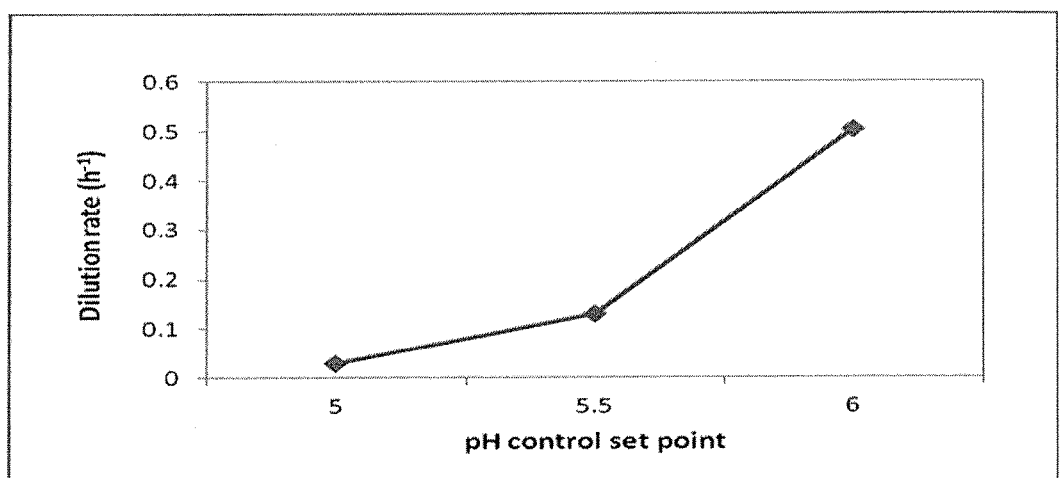
FIG. 2. The dilution rate vs. pH control set point in single stage pH-Auxostat clostridial cultures.
Figure 3:
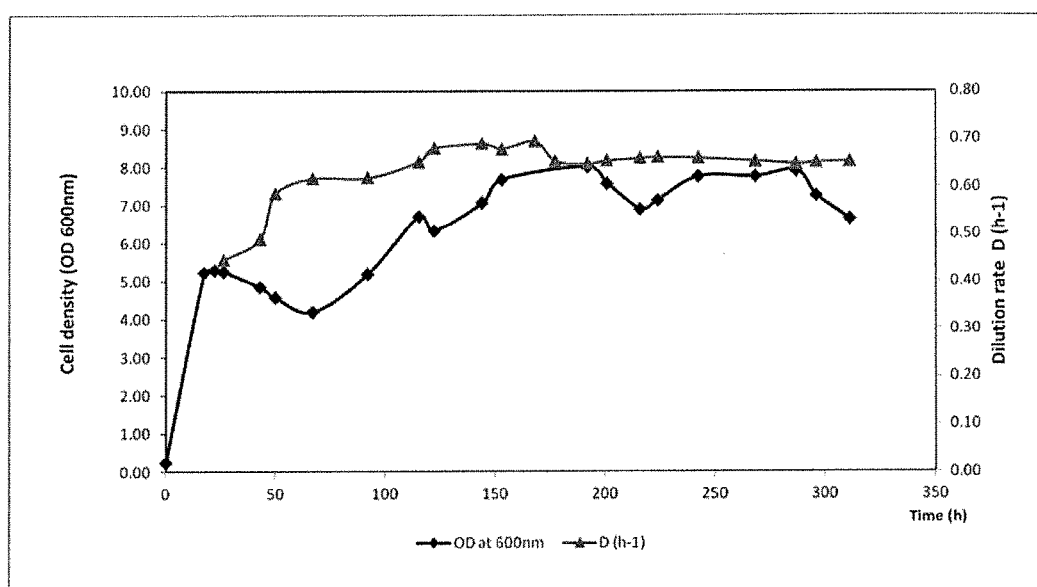
FIG. 3. The dilution rate ($h^{-1}$) and cell density (absorbance at 600 nm) in single stage pH-Auxostat clostridial cultures.

The optimal pH for the strain used was identified at 6.0. The pH value at which the fermentation was controlled was found to have a significant impact on growth rate (and consequently the dilution rate) (FIG. 2). High dilution rates were maintained for a prolonged period of time (0.49-0.69 $h^{-1}$) without culture washout suggesting the culture was growing at or close to its maximum growth rate. The residence times observed in the vessel were between 2-3 hours. There was no significant solvent production in this stage. The culture was highly stable and the cells remained healthy and viable for periods of >300 h (FIG. 3).

Example 2

Two-Stage Continuous Culture with pH-Auxostat (Stage 1) & Large Batch Vessel (Stage 2)

Objective:

To demonstrate the production of solvents at high productivity in a continuous two-stage process.

Figure 4:
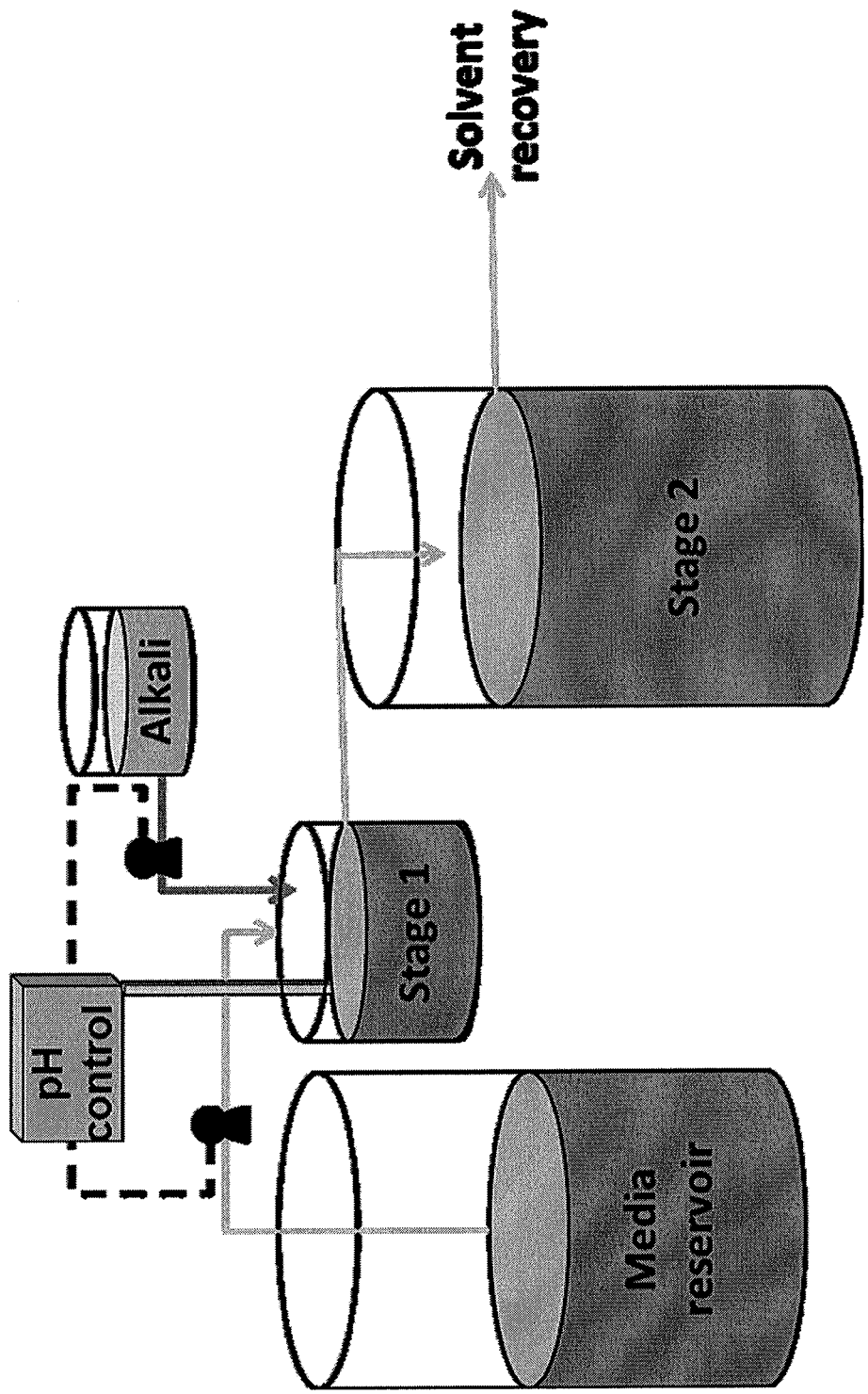
FIG. 4. Schematic diagram of Two-Stage Continuous Culture with pH-Auxostat (stage 1) & large batch vessel (stage 2).

In Example 2, the first culture vessel (pH auxostat) was identified as "Stage 1", and the media and alkali feeds were controlled by a pH auxostat ("pH controller"). The pH-Auxostat was designed to supply a consistent supply of actively growing cells into the second stage vessel, identified as "Stage 2" which was designed to produce solvents. Stage 2 consisted of a larger volume batch vessel to provide a longer residence time to complete the re-assimilation of acids to solvents (FIG. 4).

Stage 1

The pH Auxostat fermentations were carried out in 0.7 L fermenters (see Example 1).

Stage 2

The batch vessel was linked downstream of the pH-Auxostat (stage 1). The vessel was 2.8-4.8 L in volume and the temperature was controlled at 32° C. The culture pH could be controlled between pH 5.0 and 6.5 but preferably it was not controlled. The optical density of the culture (a measure of biomass concentration) was measured offline with a spectrophotometer at a wavelength of 600 nm. The sugars were measured using an HPLC, the acids and solvents were measured by GC. The culture could be sparged with $N_2$ or $CO_2$ to maintain anaerobic conditions. Preferably no special precautions were taken to exclude/remove oxygen. In this example fresh medium only entered the system through the pH auxostat, but fresh medium could also be added to any of the stage 2 vessels.

Results

A pH-Auxostat system operating at a high growth rate was initially connected to a large vertical batch vessel with a working volume of 2.7 L. The rapid growth resulted in high average dilution rates ~0.67 $h^{-1}$ (FIG. 5), with a maximum of 0.95 $h^{-1}$ at 153 h of culture. The average cell density of the culture was ~2.3 g cells $L^{-1}$ (6.8 absorbance at 600 nm) from initiation of the pH auxostat until the 13th day of culture, giving an average cell production rate of 0.024 g cells $L^{-1}$ $h^{-1}$ and a maximum cell production rate of 0.095 g cells $L^{-1}$ $h^{-1}$ at the onset of the pH-Auxostat culture. The average flow rate across the entire system (stage 1 and 2) was extremely high (0.42 L $h^{-1}$) causing low residence times (approx. 7 h) which did not allow enough time for solvents production. Average solvent concentrations of 1 g $L^{-1}$ were attained. By increasing the working volume of the second stage reactor to 4.7 L, the residence time was increased to approximately 10 h allowing more time for solvent production. This change resulted in solvent concentrations of 10 g $L^{-1}$. The longer residence times (as function of the second stage working volume) resulted in higher titres but lower productivities (Table 1).

TABLE 1

Effect of fermentation residence time on solvent titer and productivity in in two-stage continuous culture with pH-Auxostat (stage 1) & large batch vessel (stage 2)

| Fermentation residence time (h) | Solvent titer (g $L^{-1}$) | Overall fermentation productivity (g $L^{-1}h^{-1}$) |
|---|---|---|
| 6 | 1 | 0.16 |
| 10 | 9.9 | 0.99 |
| 25 | 10.22 | 0.41 |
| 49 | 15.24 | 0.31 |

Example 3

Two-Stage Continuous Culture with pH-Auxostat (Stage 1) & Sequential or Multiple Batch (Stage 2)

Objectives

Figure 6:
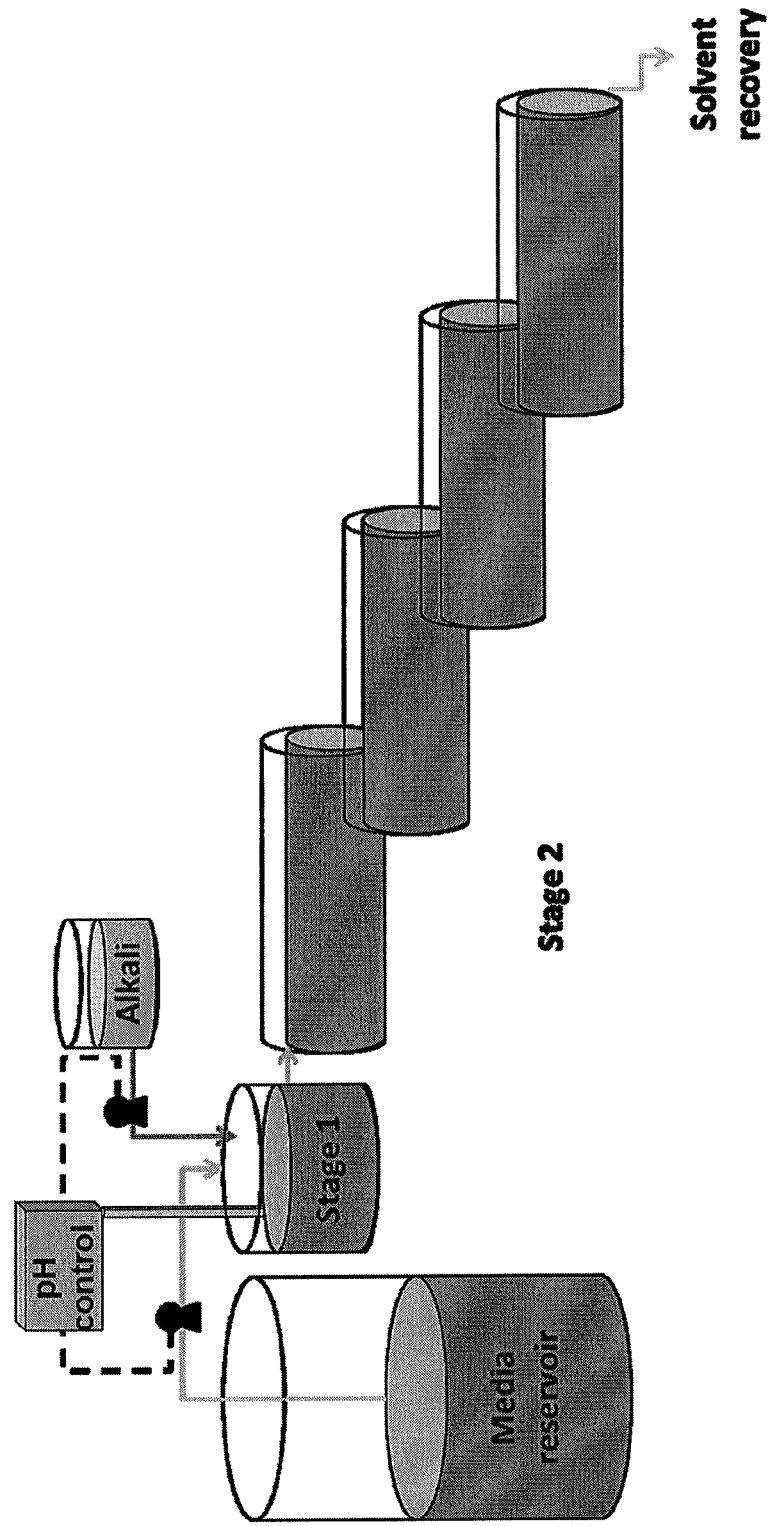
FIG. 6. Schematic diagram of two-stage continuous culture with pH-auxostat (stage 1) & horizontal sequential batch vessels (stage 2).
Figure 7:
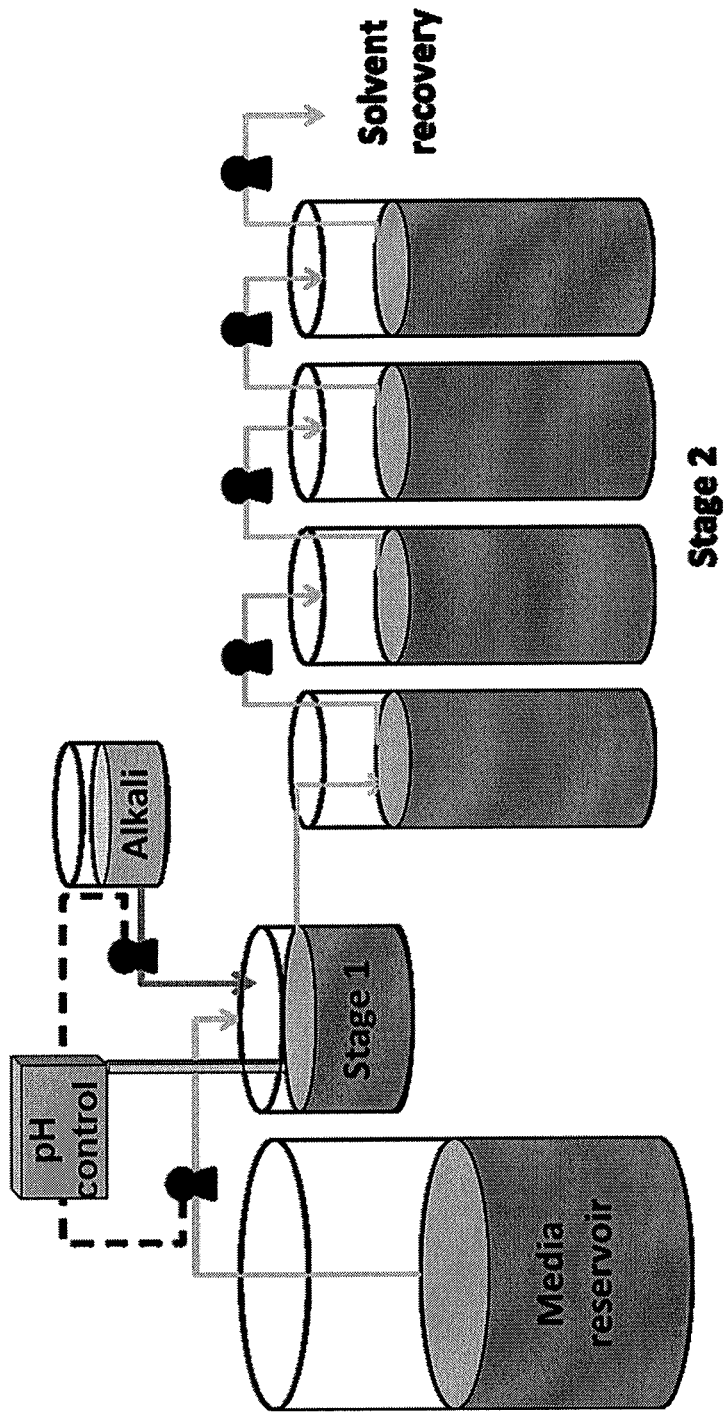
FIG. 7. Schematic diagram of two-stage continuous culture with pH-auxostat (stage 1) & vertical sequential batch vessels (stage 2).
Figure 8:
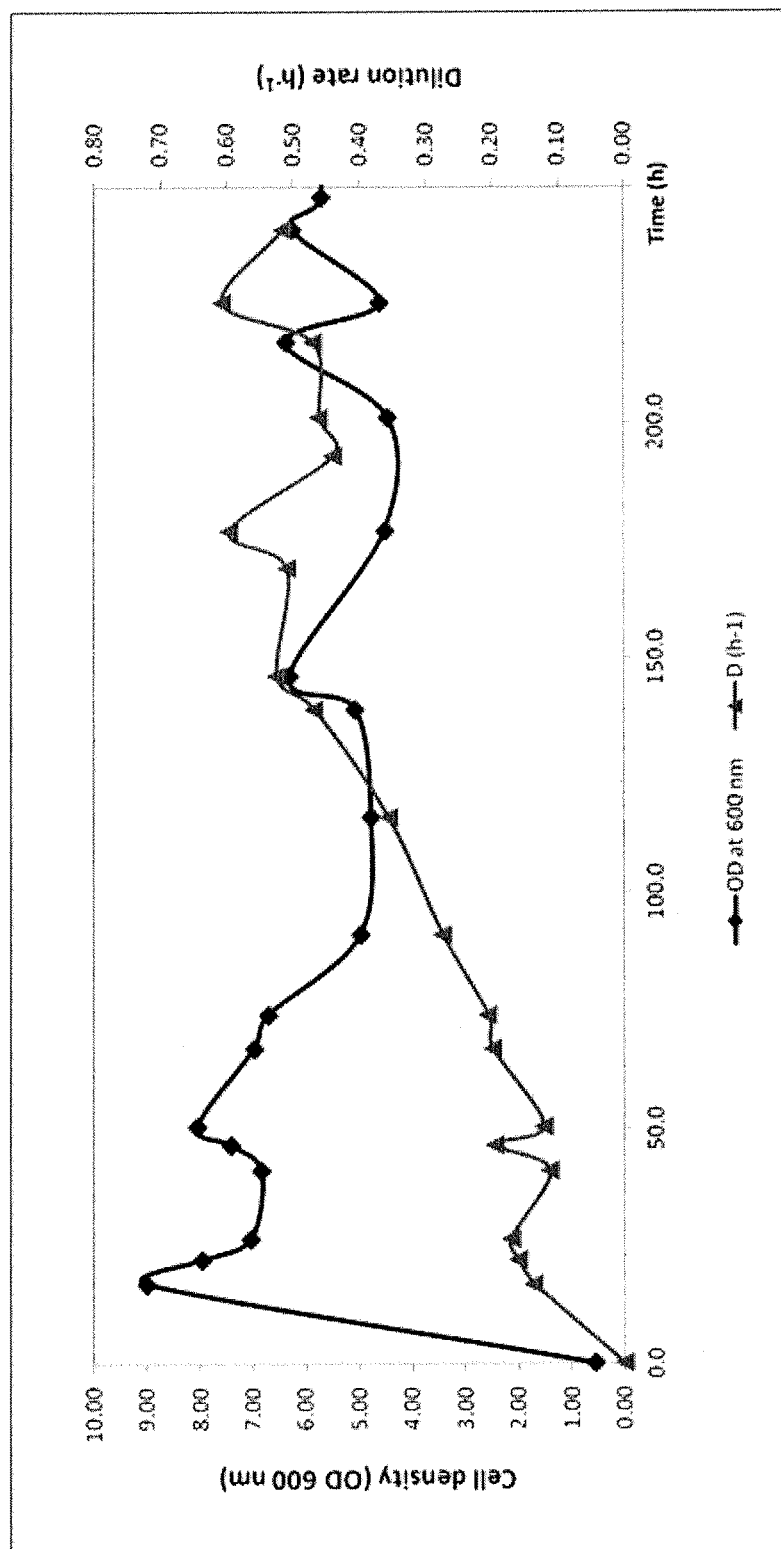
FIG. 8. Dilution rate ($h^{-1}$) and cell density (absorbance at 600 nm) in two-stage continuous culture with pH-Auxostat (stage 1) & sequential batch (stage 2).
Figure 9:
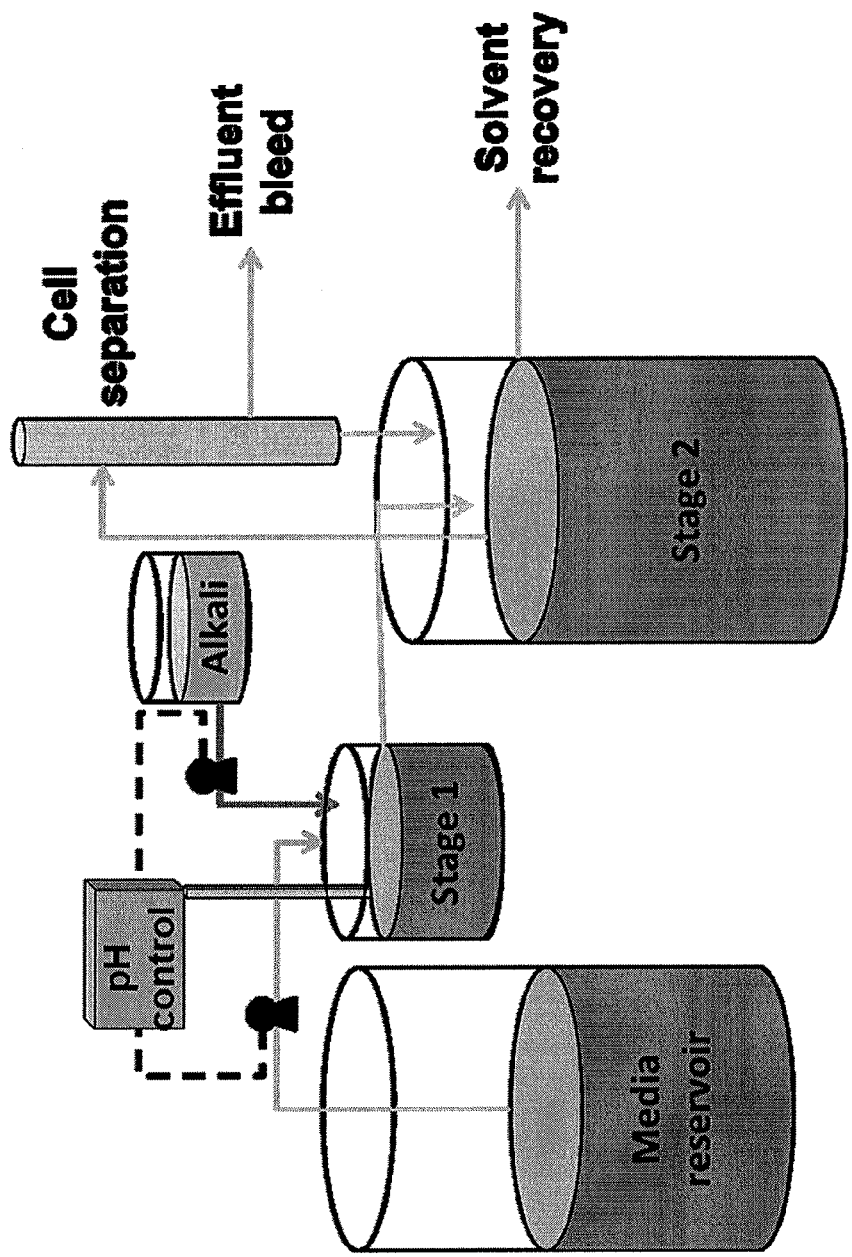
FIG. 9. Schematic diagram of Two-Stage Continuous Culture with pH-auxostat: pH-auxostat (stage 1) & large batch vessel with cell recycle (stage 2).
Figure 10:
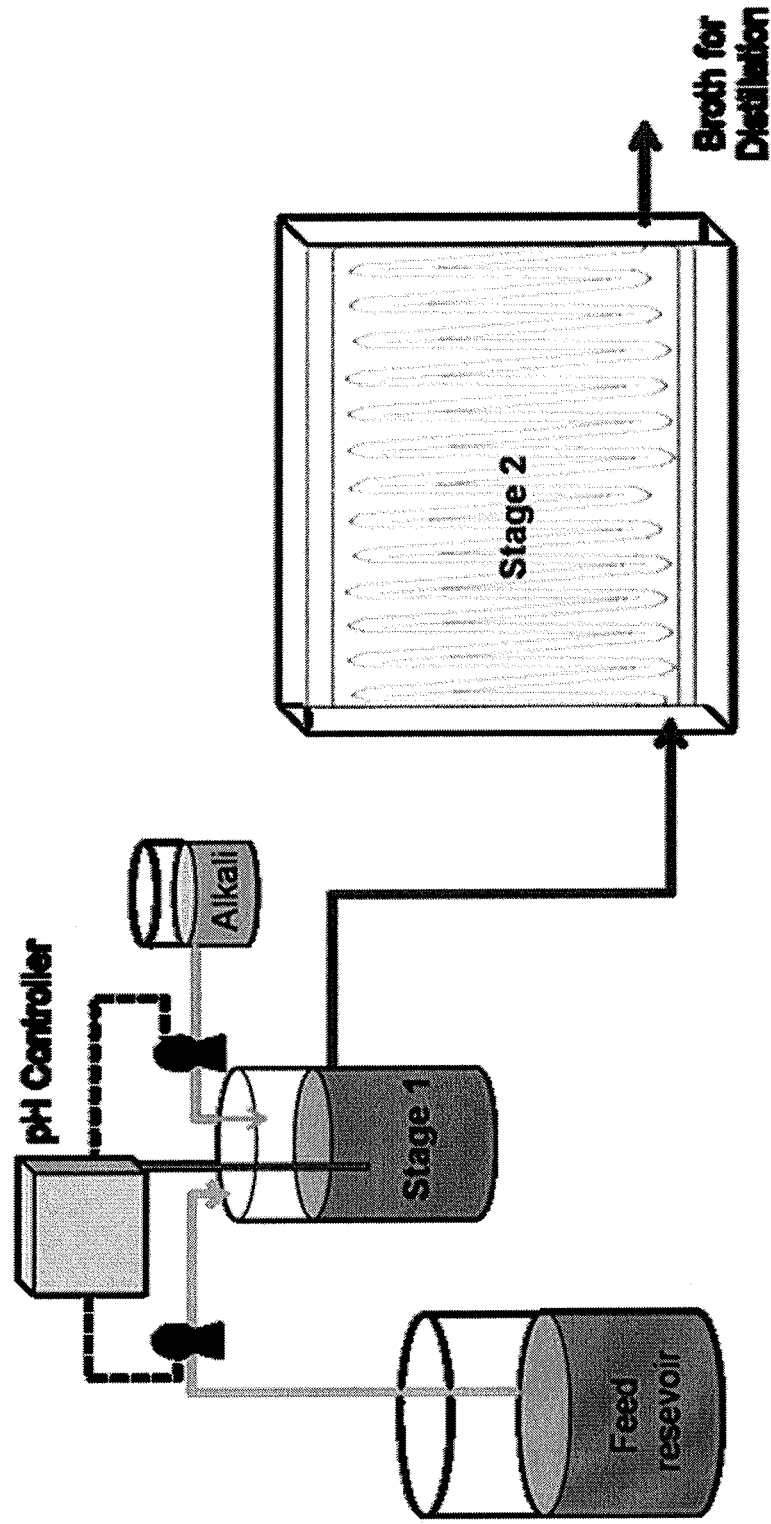
FIG. 10. Schematic diagram of Two-Stage Continuous Culture with pH-auxostat (stage 1) & tubular reactor (stage 2).
Figure 11:
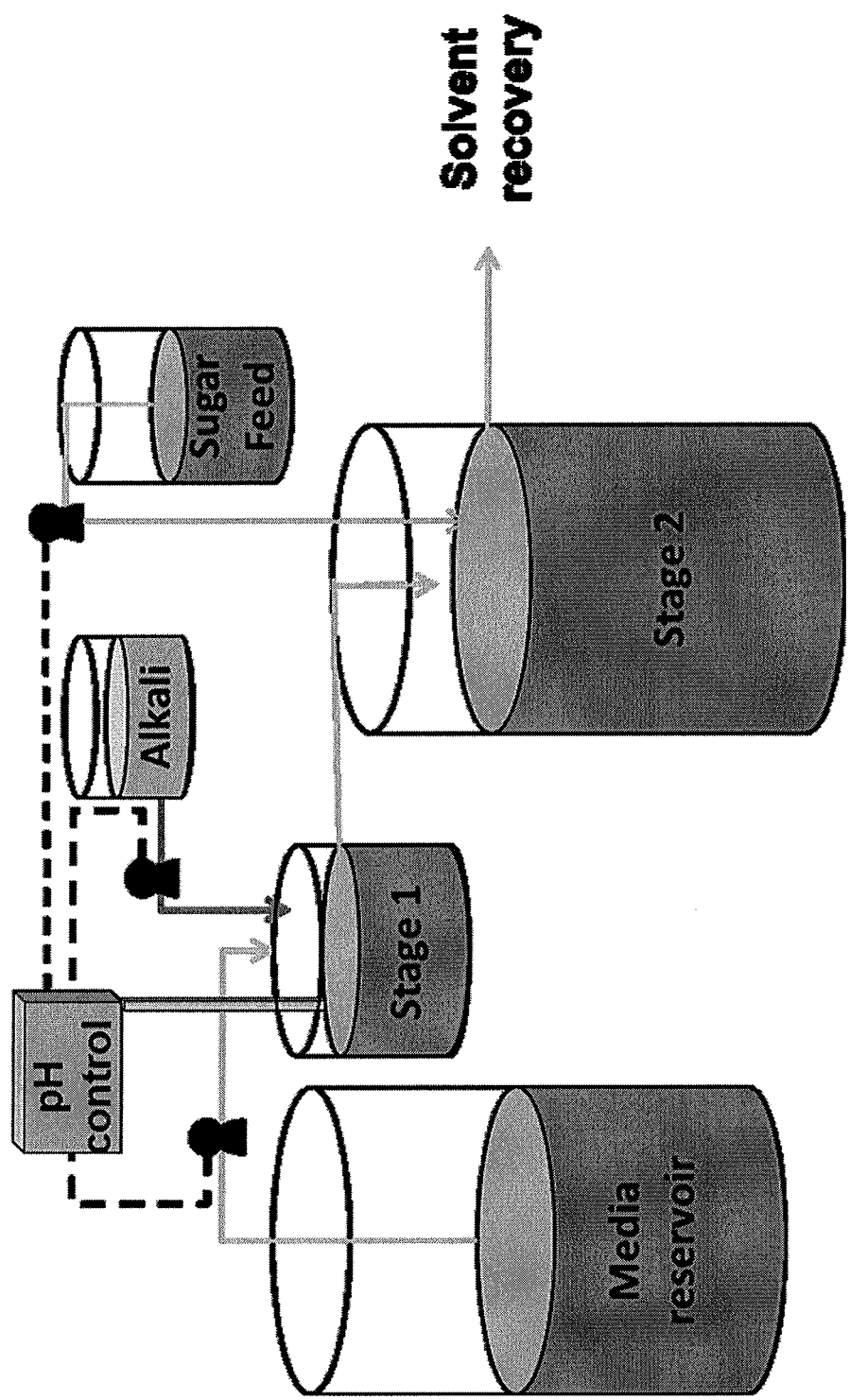
FIG. 11. Schematic diagram of Two-Stage Continuous Culture with pH-auxostat: pH-auxostat (stage 1) & large batch vessel with cell recycle (stage 2).

To demonstrate the production of solvents at high productivity in a continuous two-stage process. In Example 3, the first culture vessel (pH-Auxostat) was identified as "Stage 1", and the media feed and alkali were controlled in a pH-Auxostat mode ("pH controller"). The pH auxostat was designed to supply a consistent supply of actively growing cells into a series of vessels, identified as "Stage 2" which were designed to produce solvents. Stage 2 consisted of two or more sequential batch vessels that were aligned horizontally (FIG. 6). The vessels in stage 2 could also be aligned vertically (FIG. 7).

Stage 1

The pH-Auxostat fermentations were carried out in 0.7 L fermentors (see Example 1).

Stage 2

In this Example, two or more batch vessels were linked in series downstream of the pH Auxostat and aligned horizontally. Each vessel was 1.4 L in volume and controlled at 32° C. The culture pH could be artificially controlled between pH 5.5-6.5 but ideally it was not controlled. The optical density of the culture (a measure of biomass concentration) was measured offline with a spectrophotometer at a wavelength of 600 nm. The sugars were measured using an HPLC; the acids and solvents are measured by GC. The culture could be sparged with $N_2$ or $CO_2$ to maintain anaerobic conditions. Preferably no special precautions were taken to exclude/remove oxygen. In this example fresh medium only entered the system through the pH auxostat, but fresh medium could also be added to any stage 2 reactors.

Results

A pH-Auxostat was connected to two horizontal tubular vessels connected in series. The growth rate in the pH auxostat increased incrementally throughout the entire course of the fermentation, and the dilution rate reached a maximum of 0.39 $h^{-1}$ but due to fluctuation in the culture cultivation conditions a steady state was not attained in this case. The average cell density of the culture was ~2.2 g cells $L^{-1}$ (6.6 absorbance at 600 nm) from initiation of the pH auxostat until the 11th day of culture, giving an average cell production of 0.031 g cells $L^{-1}$ $h^{-1}$ and a maximum cell production rate of 0.166 g cells $L^{-1}$ $h^{-1}$ at the onset of the pH auxostat culture. Flow rate across both stages of 0.2 L $h^{-1}$ resulted in low residence times (9.1 h) which was not sufficient time to get acid re-assimilation and good solvent production (2.5 g $L^{-1}$). By increasing the fermentation time of the solvent production stage to 46 h (by either increasing the number of vessels linked in second stage or reducing the flow rate across the system) the average solvent titre was increased to >15 g $L^{-1}$; this also improved productivity (Table 2).

TABLE 2

Effect of fermentation residence time on solvent titer and productivity in two-stage continuous culture with pH-Auxostat (stage 1) & sequential batch (stage 2).

| Fermentation residence time (h) | Solvent titer (g $L^{-1}$) | Overall fermentation productivity (g $L^{-1}h^{-1}$) |
| --- | --- | --- |
| 9.1 | 2.5 | 0.22 |
| 26 | 9.6 | 0.34 |
| 46 | 15.91 | 0.33 |

Example 4

Two Stage (Single Batch with Cell Recycle and Concentration)

Objectives

To demonstrate increased cell density in stage 2 (fed with acidogenic cells) and increased solvent productivity whilst maintaining high dilution rates. Ideally this is linked to Example 2.

In Example 4, a two-stage process is described with cell recycle applied to stage 2 (FIG. 4). The first culture vessel is identified as "Stage 1", and the feed medium and alkali are controlled by a pH Auxostat ("pH controller"). The pH Auxostat is designed to supply a consistent supply of actively growing cells into the second stage vessel, identified as "Stage 2" which is designed to produce solvents. In "Stage 2 cell recycle is used to concentrate the cells.

Stage 1

The pH Auxostat fermentations are carried out in 0.7 L fermentors (see Example 1).

Stage 2

One batch vessel is linked downstream of the pH Auxostat. The vessel is >2 times larger than the pH-auxostat in volume (>1.4 L) and controlled at 32° C. The culture pH may be artificially controlled between pH 5.5-6.5 but ideally it is not controlled. The optical density of the culture (a measure of biomass concentration) is measured offline with a spectrophotometer at a wavelength of 600 nm. The sugars are measured using an HPLC; the acids and solvents are measured by GC. The culture may be sparged with $N_2$ or $CO_2$ to maintain anaerobic conditions. Preferably no special precautions are taken to exclude/remove oxygen. Cell recycle is performed with a hollow fibre cartridge or a similar cell concentration method with a cell bleed. Cells are separated from the culture broth and returned to the stage 2 vessel. The cell-free permeate (effluent bleed) may be recycled back to the feed reservoir. In this example fresh medium only enters the system through the pH auxostat, but fresh medium may also be added to any stage 2 reactors.

Example 5

Two Stage (Tubular Reactor)

Objectives

To demonstrate that a tubular reactor (fed with acidogenic cells) can produce solvents at high productivity.

Figure 5:
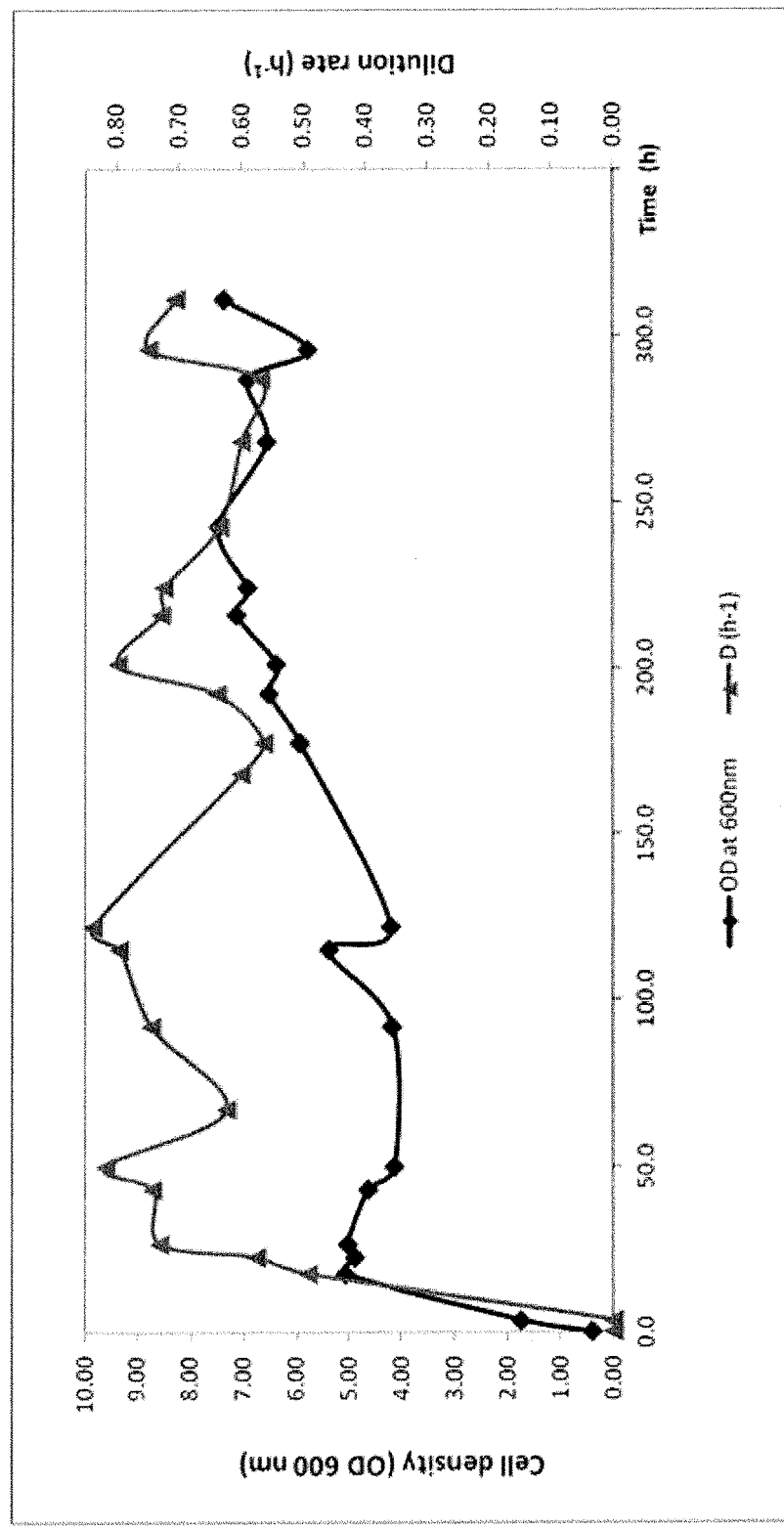
FIG. 5. Dilution rate ($h^{-1}$) and cell density (absorbance at 600 nm) in two-stage continuous culture with pH-Auxostat (stage 1) & large batch vessel (stage 2).

Example 5 is a two-stage tubular process shown in FIG. 5. The first culture vessel is identified as "Stage 1", and the liquid feed medium and alkali are controlled by a pH auxostat ("pH controller"). Stage 2 is a long tube or a series of tubes linked downstream of the pH Auxostat designed to produce sufficient residence time to complete solvent production but also to maintain the culture in "plug flow" so that the cells are exposed to the same processing conditions. The tubes may, for example be made of glass or metal.

Example 6

Two Stage (Fed-batch)

Objectives

To demonstrate that the use of a fed batch system on stage 2 (fed with acidogenic cells) to add additional sugar and/or nutrients. The aim is to increase solvent titres and productivity. Ideally stage 2 is linked to the stage 1 or Example 2.

Example 6 is a two-stage process with an additional sugar feed applied to stage 2. In this Example, the first culture vessel is identified as "Stage 1", and the liquid feed medium and alkali are controlled by a pH Auxostat ("pH controller"). The pH Auxostat is designed to supply a consistent supply of actively growing cells into the second stage vessel, identified as "Stage 2" which is designed to produce solvents. Stage 2 is a larger batch vessel linked downstream of the pH Auxostat.

The aim is to add a concentrated sugar feed (10-50%) with or without additional nutrients into stage 2. This may be deployed with or without cell recycle, preferably without.

The sugar feed may be added at a fixed rate. Preferably it is controlled in response to changes in pH and/or cell density using a pH-Auxostat or turbidostat. One option here is to link the sugar feed to the pumps controlling the alkali and media additions for stage 1 (dual Auxostat).

The invention claimed is:

1. A two-stage process for the production of a solvent using an acid- and solvent-producing micro-organism, comprising the steps:
  (i) culturing the micro-organism under acidogenic conditions in a liquid medium in a first culture vessel and using a pH auxostat to control the following:
    the pH of the liquid medium in the first culture vessel; and the flow rate of fresh media which is introduced into the first culture vessel,
wherein the pH auxostat has:
(a) separate feeds for alkali and fresh media, or
(b) a feed from fresh media that has a pH which is higher than the pH of the liquid medium in the first culture vessel;
(ii) transferring a portion of the liquid medium from the first culture vessel to a second culture vessel or series of linked culture vessels; and
(iii) culturing the same micro-organism under solventogenic conditions in the second culture vessel(s) for a time which is sufficient for solvent to be produced,
and optionally isolating one or more solvents which are produced in the second culture vessel(s).

2. A process as claimed in claim 1, wherein the micro-organism is an aero-tolerant bacterium.

3. A process as claimed in claim 1, wherein the micro-organism is a solventogenic *Clostridium*.

4. A process as claimed in claim 3, wherein the micro-organism is *Clostridium beijerinckii, Clostridium acetobutylicum, C. saccharobutylicum* or *C. saccharoperbutylacetonicum*.

5. A process as claimed in claim 1, wherein the pH of the first culture vessel is pH 5.5-7.0.

6. A process as claimed in claim 1, wherein the first culture vessel is connected directly to the second culture vessel(s), and wherein liquid media is transferred continuously from the first to the second culture vessel(s).

7. A process as claimed in claim 1, wherein the pH of the second culture vessel is pH 4.5-6.0.

8. A process as claimed in claim 1, wherein one or more of the second culture vessels is in the form of a long tubular vessel, a series of linked batch vessels or a single batch vessel.

9. A process as claimed in claim 1, wherein cells are separated from a portion of the liquid medium which has been removed from one or more of the second culture vessels and the cells are returned to one or more of the second culture vessels.

10. A process as claimed in claim 1, wherein solvent(s) are recovered from the second culture vessel by liquid-liquid extraction, gas stripping, vacuum evaporation, vacuum distillation, pervaporation, ion-exchange adsorption and/or distillation.

11. A process as claimed in claim 10, wherein the solvent extraction is by liquid extraction which is performed in situ in one or more of the second culture vessels.

12. A process as claimed in claim 1, wherein the solvent is acetone, butanol or ethanol.

* * * * *